United States Patent
Pilipski

Patent Number: 5,193,551
Date of Patent: Mar. 16, 1993

[54] PHANTOM ASSEMBLY TO VERIFY ACCURACY OF A CARBON MONOXIDE DIFFUSING CAPACITY MEASURING DEVICE

[76] Inventor: Mark Pilipski, 45 Howard Ave., Passaic Park, N.J. 07055

[21] Appl. No.: 560,851

[22] Filed: Jul. 27, 1990

[51] Int. Cl.$^5$ ............................................. A61B 5/08
[52] U.S. Cl. ................................. 128/716; 128/719; 73/1 G
[58] Field of Search ...................... 128/716, 718, 719; 73/23.2, 1 G

[56] References Cited

U.S. PATENT DOCUMENTS

| | | | |
|---|---|---|---|
| 3,948,604 | 4/1976 | Hoppesch | 73/1 G |
| 4,278,636 | 7/1981 | Voigt et al. | 422/84 |
| 4,680,956 | 7/1987 | Huszczuk | 73/1 G |

Primary Examiner—Kyle L. Howell
Assistant Examiner—Kevin Pontius
Attorney, Agent, or Firm—Michael Ebert

[57] ABSTRACT

A phantom assembly adapted to simulate a human subject to verify the accuracy of a carbon monoxide diffusing capacity (DLco) measuring device for testing the functional integrity of the subject's alveolar-capillary membrane. The device includes a mouthpiece through which the subject inhales a mixture of carbon monoxide and an inert gas in a predetermined ratio. Then after a breath holding interval the subject exhales into the mouthpiece an alveolar sample whose carbon monoxide content is analyzed by the device to evaluate the subject's condition. The assembly includes a phantom whose chamber is interposable between the mouthpiece of the DLco device and a calibration syringe having a known capacity. Within the chamber cavity is a flow tube that extends between valved mouthpiece and syringe ports on opposing end wall of the chamber. The valved port arrangements are such that when the syringe is operated in its negative pressure mode, the flow tube is then blocked and the cavity is unblocked, this blocking action being reversed when the syringe is operated in its positive pressure mode. Injected into the cavity is a given amount of inert gas whereby when the syringe is operated in its negative pressure mode, a known amount of the gas mixture is drawn from the device into the cavity where it is intermingled with the inert gas therein, thereby reducing the ratio of carbon monoxide to the inert gas to a predetermined degree to produce a test sample that fills the syringe. And when the syringe is thereafter operated in its positive pressure mode, the test sample is then expelled from the syringe and fed through the tube to the DLco device. Should the device be malfunctioning, its analysis of the sample will yield readings that deviate from the correct values, thereby indicating that the device is inaccurate.

9 Claims, 2 Drawing Sheets

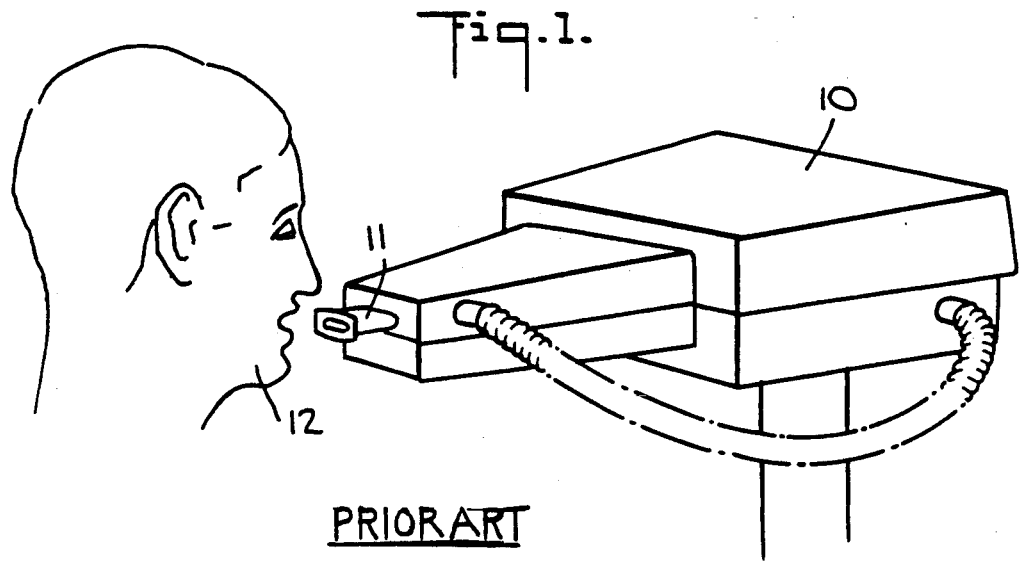
Fig. 1. PRIOR ART
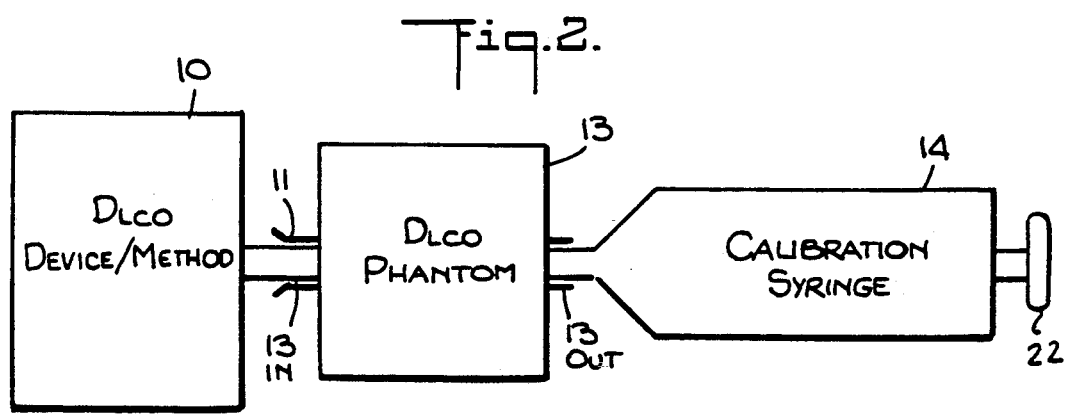
Fig. 2.
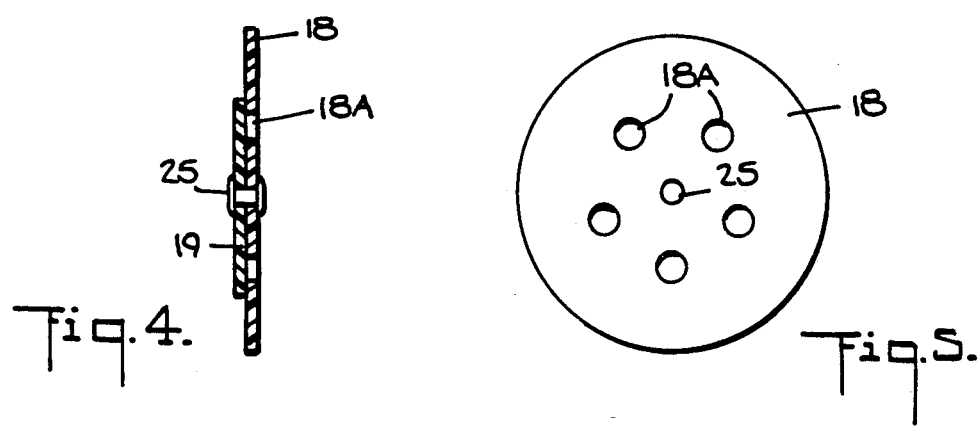
Fig. 4.
Fig. 5.

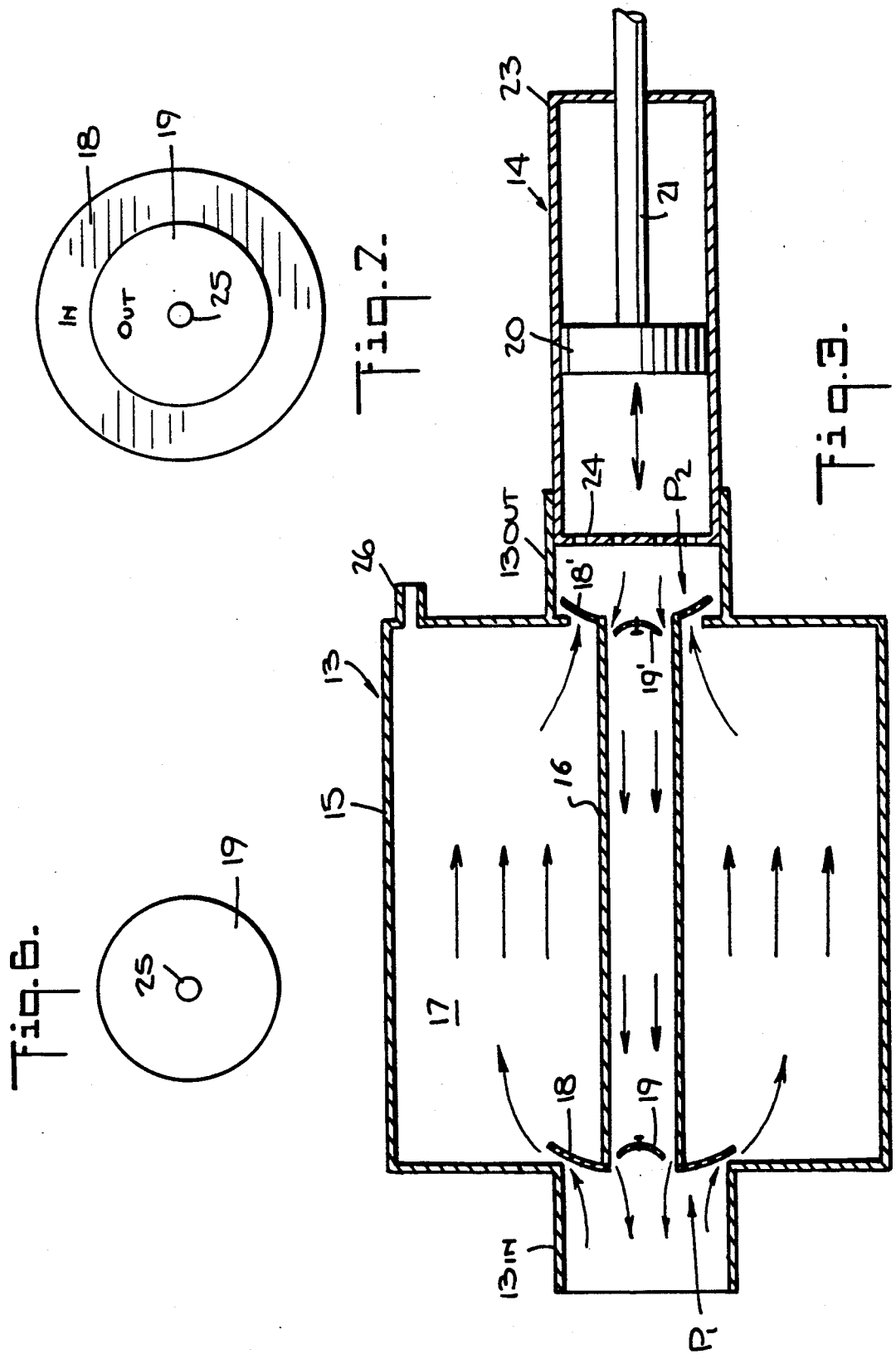

PHANTOM ASSEMBLY TO VERIFY ACCURACY OF A CARBON MONOXIDE DIFFUSING CAPACITY MEASURING DEVICE

BACKGROUND OF INVENTION

1. Field of Invention

This invention relates generally to devices adapted to test the carbon monoxide diffusing capacity (DLco) of the lungs of a human subject to determine the functional integrity of his alveolar-capillary membrane, and more particularly to a phantom assembly which simulates a human subject performing a standard DLco test and which yields a reproducible value for the DLco result, thereby making it possible to verify the accuracy of a standard DLco measuring device.

2. Status of Prior Art

The gas transfer factor for carbon monoxide (CO) is generally referred to as the pulmonary diffusing capacity (DLco). This parameter is commonly used to evaluate the transfer of gas from the distal air space into the pulmonary capillaries. The main reason why this measurement is useful in medical diagnosis is that it is the only non-invasive technique for determining the integrity of the alveolar-capillary membrane.

DLco measurement makes it possible to differentiate pathological entities that differ in the damage they inflict on the lung parenchyma, such as the reduction in alveolar-capillary surface area encountered in emphysema and changes in the permeability of the alveolar-capillary membrane as seen with diffuse interstitial processes (e.g., sarcoidosis, diffuse interstitial fibroses, and many other diseases). It is also important to understand the relationship of hemoglobin concentration and DLco in order to avoid misinterpreting a low DLco which is solely attributable to severe anemia as secondary to a non-existent lung disease.

The following references deal with the pulmonary diffusing capacity of human subjects and disclose known DLco test devices for measuring this parameter as well as clinical applications for this measurement.

1. Bates DV, Macklem PT, Christie RV; Respiratory Function in Disease, Philadelphia, WB Saunders Co., 1971, pp 93–94.
2. Forster, RE, Roughton FJW, Cander L, et al.: Apparent pulmonary diffusing capacity for CO at varying alveolar $O_2$ tensions. J. Appl Physiol 11:227–289, 1957.
3. Krumholz RA: Pulmonary membrane diffusing capacity and pulmonary capillary blood volume: An appraisal of their clinical usefulness. Am Rev Respir Dis 94:195–200, 1966.
4. Forster RE, Cohn JE, Briscoe WA, et al.: A modification of the Krogh carbon monoxide breath holding technique for estimating the diffusing capacity of the lung: A comparison with three other methods. J Clin Invest 34:1417–1426 1955.
5. Morton JW, Ostensoe LG: A critical review of the single breath method of measuring the diffusing capacity of the lungs. Dis Chest 48:44–54, 1965.
6. Cadigan JB, Marks A, Ellicott MF, et al.: An analysis of factors affecting the measurement of pulmonary diffusing capacity by the single breath method J Clin Invest 40:1495–1514, 1961.
7. Crapo RO, Morris AH: Standardized single breath normal values for carbon monoxide diffusing capacity. Am Rev Respir Dis 123:185–189, 1981.
8. Miller, A, Thornton J. C., Warshau, R, et al., single breath diffusing capacity in a representative sample of the population of Michigan. Am. Rev. Respir. Dis. 127: 270–277, 1983.

Diffusing capacity is normally measured with CO, for this gas has a high affinity for hemoglobin and is normally absent in mixed venous blood. Carbon monoxide has a membrane diffusion coefficient and a rate of reaction with hemoglobin similar to oxygen and linearly related thereto. Since carbon monoxide is normally not found in blood in appreciable amounts, this facilitates the calculation of CO uptake. And because the affinity of hemoglobin for CO is hundreds of times greater than for oxygen, a partial pressure of oxygen that remains in the physiological range is not a significant interfering factor.

The concern of the present invention is with standard devices adapted to carry out DLco measurement by the single-breath technique. In this technique, the human subject or patient who is connected to a spirometer is instructed to inhale a maximum breath (vital capacity), this inhalation starting from the end of a maximal exhalation at residual volume. In inhalation, the patient coupled to the spirometer draws into his lungs a gas mixture of soluble CO (or some other soluble gas, such as acetylene) and a non-soluble, inert tracer gas, usually neon or helium, in a predetermined ratio. The patient then holds his breath for a given number of seconds, usually 10 seconds, this being the breath holding interval or breath holding time (BHT).

When the gas mixture is inhaled by the patient, the non-soluble gas (neon or helium) will be diluted by the residual volume of air remaining at all times in the lungs, whereas the soluble gas (CO), after being diluted as the non-soluble gas and after it has diffused in the circulatory system, will be carried out of the lungs by blood flow owing to its solubility in plasma and by reason of the binding of CO to hemoglobin. The other gases present in the patient (nitrogen and oxygen) will run their usual course through the lungs as during a normal breathing process.

At the completion of the breath holding interval, the patient then proceeds to exhale into the DLco device which acts to collect an alveolar sample to be analyzed for CO concentration and inert gas concentration. The CO uptake during the holding interval can then be calculated from the inspired and expired CO concentrations and the inspired and expired inert gas concentrations. The decrease in CO concentration during the holding interval is exponential in time because the disappearance rate of CO is proportional to the concentration gradient, and this is continuously changing.

Thus a standard DLco measuring device includes means for delivery to a patient, by way of a flow pipe terminating in a mouthpiece, a gas mixture having a predetermined gas concentration of CO relative to that of an inert gas, and means for collecting and evaluating the gas exhaled by the patient into the device through the same mouthpiece.

Accurate calibration of a CO analyzer is of the utmost importance, for if the DLco device is inaccurate, then the DLco reading obtained from a given patient may be misleading and result in an improper diagnosis of his condition. Most CO analyzers are alinear in response and require multiple-point calibration. And because the degree of alinearity is subject to changes with time, full scale recalibration must be repeated on a regular basis.

When, however, a DLco device is installed in a hospital laboratory or other medical diagnostic facility, laboratory personnel who operate the device are not in a position to carry out calibration procedures and must assume that the device is accurate. Yet while this assumption may be false, heretofore the operator of the device has had no means available by which he could verify the accuracy of the DLco instrumention to be sure that test results were produced that could be relied on by the medical diagnostician.

In practice, errors may be introduced into the clinical evaluation of DLco by gas leaks in the DLco device, by faulty gas analyzers, incorrect volume measurements and improper calculation of the DLco from the data yield by the DLco device. Even with multi-point calibrations of each gas analyzer, a technically difficult procedure, and with leak checking of all gas conduits as well as verification of the accuracy of the volume measurement components, the operator of the DLco device has no means available to him to determine directly whether the DLco device is malfunctioning.

SUMMARY OF INVENTION

In view of the foregoing, the main object of this invention is to provide a method and means to carry out the method to check the accuracy of a DLco measuring device to determine whether its readings correctly reflect the carbon monoxide diffusing capacity of a human subject.

More particularly, an object of this invention is to provide a phantom assembly which simulates a human subject performing a standard DLco single-breath test, and which yields a reproducible value for the DLco result, thereby making it possible to verify the accuracy of a standard DLco measuring device.

Among the significant advantages of the invention are that the phantom assembly is of exceptionally simple design, it is inexpensive to manufacture, and it is easy to operate.

Briefly stated, these objects are attained in a phantom assembly adapted to simulate a human subject to verify the accuracy of a carbon monoxide diffusing capacity (DLco) measuring device for testing the functional integrity of the subject's alveolar-capillary membrane. The DLco device includes a mouthpiece through which the subject inhales a mixture of carbon monoxide and an inert gas in a predetermined ratio. Then after a breath holding interval, the subject exhales into the mouthpiece an alveolar sample whose carbon monoxide content is analyzed by the device to evaluate the subject's condition.

The assembly includes a phantom whose chamber is interposable between the mouthpiece of the DLco device and a calibration syringe having a known capacity. Within the chamber cavity is a flow tube that extends between valved mouthpiece and syringe ports on opposing end wall of the chamber. The valved port arrangements are such that when the syringe is operated in its negative pressure mode, the flow tube is then blocked and the cavity is unblocked, this blocking action being reversed when the syringe is operated in its positive pressure mode.

Injected into the cavity is a given amount of inert gas whereby when the syringe is operated in its negative pressure mode, a known amount of the gas mixture is drawn from the device into the cavity where it is intermingled with the inert gas therein, thereby reducing the ratio of carbon monoxide to the inert gas to a known extent to produce a test sample that fills the syringe. And when the syringe is thereafter operated in its positive pressure mode, the test sample is then expelled from the syringe and fed through the tube to the DLco device. Should the DLco device be malfunctioning, its analysis of the sample will yield readings that deviate from the correct values, thereby indicating that the device is inaccurate.

BRIEF DESCRIPTION OF DRAWINGS

For a better understanding of the invention as well as other objects and further features thereof, reference is made to the following detailed description to be read in conjunction with the accompanying drawings, wherein:

FIG. 1 illustrates a standard DLco measuring device and a human subject being tested by the device;

FIG. 2 schematically shows an assembly in accordance with the invention constituted by a phantom and a calibration syringe operatively coupled thereto;

FIG. 3 schematically illustrates the internal structure of the assembly;

FIG. 4 is a transverse section taken through one of the valve structures included in the phantom;

FIG. 5 separately shows the cavity valve element included in the structure;

FIG. 6 separately shows the flow tube valve element included in the structure; and FIG. 7 is a front view of the valve structure.

DESCRIPTION OF INVENTION

Referring now to FIG. 1, there is shown a standard, single breath DLco measuring device 10 provided with a mouthpiece 11 to be engaged by the mouth of a human subject or patient 12 to be tested.

Because of the ease and non-invasive nature of the single breath technique for determining the diffusing capacity of the human subject, this test is widely used to assess carbon monoxide transfer. To conduct a test, patient 12 inhales through mouthpiece 11 a gas mixture containing soluble carbon monoxide (CO) and an inert, non-soluble gas, preferably helium (He). Before inhaling this mixture, the patient exhales to residual volume and he then inhales to total lung capacity a gas mixture typically containing 0.3 percent CO, 10 percent He, 20 percent oxygen, the remainder being nitrogen. Then the patient holds his breath for a predetermined holding interval, e.g., 10 seconds. At the conclusion of this breath holding interval, the patient exhales into the mouthpiece an alveolar sample which is analyzed in the device.

In order to determine the amount of CO transferred across the patient's membrane, the concentration CO must be measured at the beginning and end of the 10-second breath holding interval. The concentration at the end of the interval is measured by monitoring the expired CO concentration and taking a value near the end of expiration, this value representing alveolar gas. The concentration at the beginning of the breath holding interval must be determined indirectly, as the concentration of inhaled CO is diluted by the residual volume in the lungs and therefore cannot be directly measured.

Calculation of this dilution is performed by measuring the concentration of helium at the beginning and end of the breath holding interval. Because helium is not transferred across the alveolar-capillary interface to a significant degree, any dilution in helium concentration is attributable to dilution in the lungs.

The known data from which DLco is evaluated are the following values: (1) volume inspired, (2) length of breath holding interval, (3) initial concentration of helium, (4) initial concentration of carbon monoxide, (5) final concentration of helium and (6) final concentration of carbon monoxide.

However, as previously noted, errors may be introduced into the clinical evaluation of DLco by gas leaks in DLco device 10, by faulty gas analyzers and incorrect volume measurement, as well as erroneous calculations of DLco from the available data.

In order to verify the accuracy of DLco measuring device 10, the function of a human subject is simulated, as shown in FIG. 2, by an assembly including a phantom 13 whose input coupler 13*in* is coupled to mouthpiece 11 of the DLco device, and whose output coupler 13*out* is operatively coupled to a calibration syringe 14. In simulating a human subject performing a DLco test, phantom 13 yields a reproducible value for the DLco result. The actual value obtained may be fixed within the normal range of expected values to validate the accuracy of the DLco measuring device.

Calibration syringe 14 is of the piston type conventionally used in a pulmonary laboratory and has a precisely known volume, say, 3 liters. When, therefore, the piston is fully retracted to produce a negative pressure, three liters of gas are drawn into the syringe. And when the piston is fully advanced, the resultant positive pressure expels the 3 liters of gas from the syringe. Such calibration syringes are commonly employed to provide a known volume of gas to verify gas volume measurement devices, such as spirometers, pneumo tachs and volumeters.

As shown in FIG. 3, DLco phantom 13 is provided with a chamber 15 having a flow tube 16 coaxially disposed therein. Tube 16 extends the full length of the chamber between valved ports $P_1$ and $P_2$ arranged on opposing end walls of the chamber. Surrounding tube 16 in the chamber is a cavity 17 which in practice may have a volume of about 2 liters which is less than the 3 liter capacity of calibration syringe 14.

The phantom input coupler 13*in* leads to port $P_1$ and is coupled thereby to one end of cavity 17 by a unidirectional valve element 18 and is also coupled to the corresponding end of flow tube 16 by a unidirectional valve element 19 which is reversely biased. Hence a positive pressure, which causes valve element 18 to close, simultaneously causes valve element 19 to open.

The phantom output coupler 13*out* leads to valved port $P_2$ and is coupled thereby to the other end of cavity 17 by a unidirectional valve element 18' and is also coupled to the corresponding end of flow tube 16 by a reversely-biased valve element 19'.

Calibration syringe 14 which is operatively coupled to output 13*out* of chamber 13 is provided with a piston 20 which is connected by a piston rod 21 to a handle 22. Piston 20 is slidable within a barrel 23 whose leading end is closed by an apertured disc 24.

When syringe 14 is operated in its negative pressure mode by retracting piston 20, the resultant negative pressure causes port valves 18 and 18' to open, thereby drawing a gas mixture from input 13*in* coupled to the DLco device 10 into cavity 17 of the phantom and from cavity 17 into the syringe. The volume of the gas mixture so drawn depends on the capacity of the syringe.

In the negative mode of the syringe, the negative pressure acts to close valve elements 19 and 19', thereby blocking flow tube 16 at both ends thereof. When, however, syringe 14 is operated at its positive pressure mode by advancing piston 20 toward apertured disc 24, then this positive gas pressure causes valve elements 18 and 18' to shut to block access to cavity 17, while at the same time causing valve elements 19 and 19' to open to unblock flow tube 16. As a consequence, in its positive pressure mode, gas in syringe 14 is forced through flow tube 16 into the DLco device coupled to input 13*in*.

In a preferred embodiment of the valve structure as shown in FIGS. 4 to 7, the valve element 18 (or 18') for controlling flow into cavity 17 is formed by a rubber disc of large diameter having a circular array of apertures 18A surrounding its center, disc 18 being secured at its center by a rivet 25 to a rubber disc 19 of smaller diameter which overlies the array of apertures 18A. The valve structure formed by discs 18 and 19 is mounted on an end of tube 16 by a suitable spider (not shown). In practice, it is not necessary that both ports $P_1$ and $P_2$ be valved, for it is sufficient to valve only port $P_1$.

Before putting the phantom assembly into operation, syringe 14 has its piston 20 fully advanced so that barrel 23 is then empty. A bolus of helium of known volume, or whatever other inert gas (such as neon) is used in the DLco device, is injected into cavity 17 of phantom 13 through a closable inlet 20 to provide a reference. When syringe 14 is then operated in its negative pressure mode and piston 20 is fully withdrawn, three liters (the capacity of the syringe) of the CO-He gas mixture in DLco device 20 is sucked into cavity 17 to intermingle therein with the reference helium.

The CO-He mixture drawn from the device 10 into cavity 17 and into syringe 14 has a predetermined ratio; but since this mixture is intermingled with the reference volume of helium injected into the cavity and the air present in the cavity, this ratio is altered to a known degree.

If, therefore, the DLco device is functioning accurately, the extent to which the ratio of the gas mixture has been altered by the phantom assembly which simulates a human subject will be correctly reflected in the readings of the device. And each time the device is checked by the phantom, the same readings should be obtained.

However, if the DLco inspired or expired volume is not equal to the volume of the calibration syringe, this would indicate that the device is not measuring volume correctly. And if the initial helium concentration or the measured final concentration of helium does not match the concentration of helium supplied or the calculated final helium concentration, this is indicative of an error in the helium analyzer. This also applies to errors in the reading of carbon monoxide concentration.

The final DLco value obtained by the user of the DLco phantom will remain constant (within experimental error tolerances) from test to test unless the DLco device is malfunctioning. Therefore, the DLco value obtained using the DLco phantom is an index to the accuracy of the DLco measuring device.

To inject an exact amount of reference helium into the cavity of the chamber, one may use an external syringe for this purpose. Or the helium may be contained under pressure in a cartridge that when screwed into an inlet port of the phantom discharges the helium into the cavity.

While there has been shown and described a preferred embodiment of a phantom assembly to verify accuracy of DLco measuring device in accordance with the invention, it will be appreciated that many changes and modifications may be made therein without, however, departing from the essential spirit thereof.

I claim:

1. A phantom assembly adapted to simulate a human subject to verify the accuracy of a carbon monoxide diffusing capacity measuring device to test the functional capacity of the subject's alveolar-capillary membrane, said device including a mouthpiece through which the subject inhales a mixture of carbon monoxide and an inert gas in a predetermined ratio, the subject after a breath holding interval exhaling into the mouthpiece an alveolar sample whose carbon monoxide content is analyzed, said assembly comprising:

(a) a phantom provided with a chamber having respective ports at opposing ends thereof, and a flow tube disposed within the chamber and extending between the ports, the tube being surrounded by a cavity having a predetermined volume of said inert gas injected therein;

(b) a calibration syringe having a negative pressure mode in which the pressure causes a gas to fill the syringe and a positive pressure mode in which the pressure expels the gas, and (c) means for coupling one of said ports to said device, and the other of said ports to said syringe whereby when said syringe is operated in the negative pressure mode, said tube is blocked and said gas mixture is drawn into said cavity and said syringe to intermingle with said inert gas to alter its ratio to a known degree to produce a test sample, and when said syringe is operated in the positive pressure mode, said cavity is then blocked and said test sample is forced through said tube into said device which will then yield a reading that deviates from a calculable and predictable value only if the device is malfunctioning.

2. An assembly as set forth in claim 1, wherein said inert gas is helium.

3. An assembly as set forth in claim 1, wherein said calibration syringe includes a piston slidable in a barrel from a retracted position at one end of the barrel to an advanced position at its other end.

4. An assembly as set forth in claim 1, wherein said chamber is coupled to the mouthpiece of the device by an input coupler and to the syringe by an output coupler.

5. An assembly as set forth in claim 1, wherein each port is provided with a first unidirectional valve element at the related end of the tube which is caused to open only when subjected to positive pressure and a second unidirectional valve element concentric with the tube at the related end of the cavity which is caused to open only when subjected to negative pressure.

6. An assembly as set forth in claim 1, wherein said first and second valve elements are formed by rubber discs.

7. An assembly as set forth in claim 6, wherein said discs are joined together at their center by a rivet.

8. A method for simulating a human subject to verify the accuracy of a carbon monoxide diffusing capacity measuring device to test the functional capacity of the subject's alveolar-capillary membrane, said device including a mouthpiece through which the subject inhales a mixture of carbon monoxide and an inert gas in a predetermined ratio, the subject after a breath holding interval exhaling into the mouthpiece an alveolar sample whose carbon monoxide content is analyzed, said method comprising the steps of:

(a) injecting into a phantom chamber a known volume of said inert gas:

(b) drawing from said mouthpiece a predetermined volume of said mixture of carbon monoxide and said inert gas, and feeding the mixture into the phantom chamber to intermingle with the inert gas therein, whereby said mixture ratio is then altered to a known degree to provide in said chamber a test sample simulating a human subject; and (c) feeding the test sample into the device through the mouthpiece and causing the device to analyze the test sample to yield a reading that will deviate from a calculable and predictable value only if the device is malfunctioning.

9. A method as set forth in claim 8, wherein said inert gas is helium.

* * * * *